United States Patent
Kassahun et al.

(10) Patent No.: US 8,791,162 B2
(45) Date of Patent: Jul. 29, 2014

(54) CATHEPSIN CYSTEINE PROTEASE INHIBITORS

(75) Inventors: Kelem Kassahun, Collegeville, PA (US); Christine Fandozzi, North Wales, PA (US); Donald R. Gauthier, Jr., Westfield, NJ (US); Lisa A. Shipley, Harleysville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/984,877

(22) PCT Filed: Feb. 9, 2012

(86) PCT No.: PCT/US2012/024391
§ 371 (c)(1),
(2), (4) Date: Aug. 12, 2013

(87) PCT Pub. No.: WO2012/112363
PCT Pub. Date: Aug. 23, 2012

(65) Prior Publication Data
US 2013/0324610 A1   Dec. 5, 2013

Related U.S. Application Data

(60) Provisional application No. 61/442,368, filed on Feb. 14, 2011.

(51) Int. Cl.
*A61K 31/277* (2006.01)
*C07C 255/46* (2006.01)

(52) U.S. Cl.
CPC ............. *C07C 255/46* (2013.01); *A61K 31/277* (2013.01)

USPC ............................................ 514/618; 558/426

(58) Field of Classification Search
CPC ............................ A61K 31/277; C07C 255/46
USPC ............................................ 514/618; 558/426
See application file for complete search history.

(56) References Cited

U.S. PATENT DOCUMENTS

| 6,596,715 | B1 | 7/2003 | Marquis, Jr. et al. |
| 7,375,134 | B2 | 5/2008 | Bayly et al. |

FOREIGN PATENT DOCUMENTS

WO    WO03/075836    9/2003

OTHER PUBLICATIONS

Isabel, et. al., "The discovery of MK-0674, an orally bioavailable cathepsin K inhibitor", Bioorganic and Medicinal Chemistry Letters, 2010, vol. 20, pp. 887-892.
Stoch, et. al, "Effect of the Cathepsin K Inhibitor Odanacatib on Bone Resorption Biomarkers in Healthey Postmenopausal Women: Two Double-Blind, Randomized, Placebo-Controlled Phase 1 Studies", Clinical Pharmacaology & Therapeutics, vol. 86, No. 2, Aug. 2009.
PCT International Search Report for PCT/US/12/24391 dated May 23, 2012, 2 pages.
Written Opinion for PCT International App. No. PCT/US/12/24391 dated May 23, 2012, 2 pages.

*Primary Examiner* — Samantha Shterengarts
(74) *Attorney, Agent, or Firm* — Nicole M. Beeler; Catherine D. Fitch (57) ABSTRACT

This invention relates to deuterated compounds which are useful for treating diseases in which inhibition of bone resorption is indicated, such as osteoporosis.

6 Claims, 2 Drawing Sheets

CATHEPSIN CYSTEINE PROTEASE INHIBITORS

BACKGROUND OF THE INVENTION

Cathepsin K (Cat K) is a lysosomal cysteine protease that is highly expressed in osteoclasts, the cells responsible for bone degradation during bone remodeling. Type I collagen is a major component of bone and Cat K has high collagenase activity, particularly at the acidic pH that is require to dissolve the calcium hydrocyapatite component of bone. Emerging evidence that Cat K is the primary enzyme involved in osteoclastic bone resorption has made it an important target for the treatment of osteoporosis. Several studies have shown that cat K deficiency leads to an increase in bone mineral density (BMD). Pharmacological studies of Cat K inhibitors in rats and monkeys have shown reductions in biochemical markers of bone resorption and increased BMD (See, e.g. Barrett, F. G. et al., *Bioorg. Med. Lett.* 12005, 15, 3540; Kumar, S, et al., *Bone*, 2007, 40, 122).

A variety of cathepsin K inhibitors have been disclosed for the treatment of various disorders related to cathepsin K functioning, including osteoporosis, glucocorticoid induced osteoporosis, Paget's disease, abnormally increased bone turn over, tooth loss, bone fractures, rheumatoid arthritis, osteoarthritis, periprosthetic osteolysis, osteogenesis imperfecta, atherosclerosis, obesity, glaucoma, chronic obstructive pulmonary disease and cancer including metastatic bone disease, hypercalcemia of malignancy, and multiple myeloma. Representative examples of cathepsin K inhibitors, are disclosed in International Publication WO03/075836, which published on Sep. 18, 2003, to Merck & Co., Inc. & Axys Pharmaceuticals, which is hereby incorporated by reference in its entirety.

A particularly effective cathepsin K inhibitor is $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide, which can be prepared by procedures described in: International Publication WO03/075836, which published on Sep. 18, 2003, to Merck & Co., Inc. & Axys Pharmaceuticals; International Publication WO2006/017455, which published on Feb. 16, 2006, to Merck & Co., Inc.; U.S. Publication US2006-0052642, which published on Mar. 9, 2006; U.S. Publication US2005-0234128, which published on Oct. 20, 2005, to Merck & Co., Inc.; all of which are hereby incorporated by reference in their entirety. This compound is also known by its generic name, odanacatib.

Odanacatib, is an orally active, potent and selective Cat K inhibitor currently in development for the treatment of post-menopausal osteoporosis. Odanacatib inhibits human Cat K and has ≥300-fold selectivity against all other known human cathepsins. Studies have shown that odanacatib is well tolerated, and has shown suppression of bone resorption biomarkers when administered in daily and weekly regimens (See, Stoch, S. A. et al., *Clinical Pharmacology & Therapeutics*, 2009, 86, 175).

It would be desirable to reduce the rate of metabolism of odanacatib. By developing a deuterium substituted analogue of odanacatib, the clearance of the drug can be reduced, thus creating the potential for a drug with a longer half-life.

SUMMARY OF THE INVENTION

The present invention relates to compounds that are capable of treating and/or preventing cathepsin dependent conditions or disease states in a mammal in need thereof. One embodiment of the present invention is illustrated by a compound of Formula I, and the pharmaceutically acceptable salts, stereoisomers and N-oxide derivatives thereof:

DETAILED DESCRIPTION OF THE INVENTION

The present invention relates to compounds of the following chemical formula:

wherein each X is independently deuterium or hydrogen, and greater than 90% of the compound has a deuterium atom at each position designated as deuterium, and any atom not designated as deuterium is present at its natural abundance; or a pharmaceutically acceptable salt thereof.

In a class of the invention of formula I, one X is deuterium. In a class of the invention of formula I, two Xs are deuterium. In a class of the invention of formula I, three Xs are deuterium. In a class of the invention of formula I, four Xs are deuterium. In a class of the invention of formula I, each X is deuterium.

Reference to the preferred embodiments set forth above is meant to include all combinations of particular and preferred groups unless stated otherwise.

Specific embodiments of the present invention include, but are not limited to:

Compound 14 wherein greater than 90% of the compound has a deuterium atom at each position designated as deuterium, and any atom not designated as deuterium is present at its natural abundance, or a pharmaceutically acceptable salt or stereoisomer thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The present invention also relates to compounds of the following chemical Formula II:

II wherein each X is independently deuterium or hydrogen, and greater than 90% of the compound has a deuterium atom at each position designated as deuterium, and any atom not designated as deuterium is present at its natural abundance; or a pharmaceutically acceptable salt thereof.

In a class of the invention of formula II, one X is deuterium. In a class of the invention of formula II, two Xs are deuterium.

Reference to the preferred embodiments set forth above is meant to include all combinations of particular and preferred groups unless stated otherwise.

Specific embodiments of the present invention include, but are not limited to:

Compound 24 wherein greater than 90% of the compound has a deuterium atom at each position designated as deuterium, and any atom not designated as deuterium is present at its natural abundance, or a pharmaceutically acceptable salt or stereoisomer thereof.

The present invention also relates to compounds of the following chemical Formula

III wherein each X is independently deuterium or hydrogen, and greater than 90% of the compound has a deuterium atom at each position designated as deuterium, and any atom not designated as deuterium is present at its natural abundance; or a pharmaceutically acceptable salt thereof.

In a class of the invention of formula III, one X is deuterium. In a class of the invention of formula III, two Xs are deuterium. In a class of the invention of formula III, three Xs are deuterium. In a class of the invention of formula III, four Xs are deuterium. In a class of the invention of formula III, five Xs are deuterium. In a class of the invention of formula III, six Xs are deuterium. In a class of the invention of formula III, each X is deuterium.

Reference to the preferred embodiments set forth above is meant to include all combinations of particular and preferred groups unless stated otherwise.

Specific embodiments of the present invention include, but are not limited to:

wherein greater than 90% of the compound has a deuterium atom at each position designated as deuterium, and any atom not designated as deuterium is present at its natural abundance, or a pharmaceutically acceptable salt or stereoisomer thereof.

Utilities

The compounds of the present invention are inhibitors of cathepsins and are therefore useful to treat or prevent cathepsin dependent diseases or conditions in mammals, preferably humans. Specifically, the compounds of the present invention are inhibitors of Cathepsin K and are therefore useful to treat or prevent Cathepsin K dependent diseases or conditions in mammals, preferably humans.

The compounds of the present invention have advantages over structurally similar compounds known in the art in that they have a marked improved metabolic and pharmacokinetic profiles. Specifically, the deuterated compounds of the instant invention have reduced cytochrome P450-mediated clearance when compared to the non-deuterated analogs. Compared to unmodified odanacatib, deuterium substitution resulted in a decrease in the rate of clearance of 70% and an increase in AUC and half-life.

"Cathepsin dependent diseases or conditions" refers to pathologic conditions that depend on the activity of one or more cathepsins. "Cathepsin K dependent diseases or conditions" refers to pathologic conditions that depend on the activity of Cathepsin K. Diseases associated with Cathepsin K activities include osteoporosis, glucocorticoid induced osteoporosis, Paget's disease, abnormally increased bone turnover, tooth loss, bone fractures, rheumatoid arthritis, osteoarthritis, periprosthetic osteolysis, osteogenesis imperfecta, atherosclerosis, obesity, glaucoma, chronic obstructive pulmonary disease and cancer including metastatic bone disease, hypercalcemia of malignancy, and multiple myeloma. In treating such conditions with the instantly claimed compounds, the required therapeutic amount will vary according to the specific disease and is readily ascertainable by those skilled in the art. Although both treatment and prevention are contemplated by the scope of the invention, the treatment of these conditions is the preferred use.

An embodiment of the invention is a method of inhibiting cathepsin activity in a mammal in need thereof, comprising administering to the mammal a therapeutically effective amount of any of the compounds or any of the pharmaceutical compositions described above.

A class of the embodiment is the method wherein the cathepsin activity is cathepsin K activity.

Another embodiment of the invention is a method of treating or preventing cathepsin dependent conditions in a mammal in need thereof, comprising administering to the mammal a therapeutically effective amount of any of the compounds or any of the pharmaceutical compositions described above.

A class of the embodiment is the method wherein the cathepsin activity is cathepsin K activity.

Another embodiment of the invention is a method of inhibiting bone loss in a mammal in need thereof, comprising administering to the mammal a therapeutically effective amount of any of the compounds or any of the pharmaceutical compositions described above. Another embodiment of the invention is a method of reducing bone loss in a mammal in need thereof, comprising administering to the mammal a therapeutically effective amount of any of the compounds or any of the pharmaceutical compositions described above. The utility of cathepsin K inhibitors in the inhibition of bone resorption, which includes abnormally increased bone turnover, bone fractures, Paget's disease, osteogenesis imperfecta and periprosthetic osteolysis, is known in the literature, see Stroup, G. B., Lark, M. W., Veber, D F., Bhattacharrya, A., Blake, S., Dare, L. C., Erhard, K. F., Hoffman, S. J., James, I. E., Marquis, R. w., Ru, Y., Vasko-Moser, J. A., Smith, B. R., Tomaszek, T. and Gowen, M. Potent and selective inhibition of human cathepsin K leads to inhibition of bone resorption in vivo in a nonhuman primate. J. Bone Miner. Res., 16:1739-1746; 2001; and Votta, B. J., Levy, M. A., Badger, A., Dodds, R. A., James, I. E., Thompson, S., Bossard, M. J., Carr, T., Connor, J. R., Tomaszek, T. A., Szewczuk, L., Drake, F. H., Veber, D., and Gowen, M. Peptide aldehyde inhibitors of cathepsin K inhibit bone resorption both in vivo and in vitro. J. Bone Miner. Res. 12:1396-1406; 1997.

Another embodiment of the invention is a method of treating or preventing osteoporosis, including glucocorticoid induced osteoporosis, in a mammal in need thereof, comprising administering to the mammal a therapeutically effective amount of any of the compounds or any of the above pharmaceutical compositions described above. The utility of cathepsin K inhibitors in the treatment or prevention of osteoporosis is known in the literature, see Saftig, P., Hunziker, R, Wehmeyer, O., Jones, S., Boyde, A., Rommerskirch, W., Moritz, J. D., Schu, P., and Vonfigura, K. Impaired osteoclast bone resorption leads to osteopetrosis in cathepsin K-deficient mice. Proc. Natl. Acad. Sci. USA 95:13453-13458; 1998.

Another embodiment of the invention is a method of treating or preventing periodontal disease, including tooth loss, in a mammal in need thereof, comprising administering to the mammal a therapeutically effective amount of any of the compounds or any of the above pharmaceutical compositions described above. The utility of cathepsin K inhibitors in the treatment or prevention of periodontal disease and tooth loss is known in the literature, see Tsuji Y, et al., Expression of cathepsin K mRNA and protein in odontoclasts after experimental tooth movement in the mouse maxilla by in situ hybridization and immunoelectron microscopy. Cell Tissue Res. 2001 March; 303(3):359-69.

Another embodiment of the invention is a method of treating or preventing rheumatoid arthritic condition in a mammal in need thereof, comprising administering to the mammal a therapeutically effective amount of any of the compounds or any of the pharmaceutical compositions described above. It is known in the literature that progressive destruction of the periarticular bone is a major cause of joint dysfunction and disability in patients with rheumatoid arthritis (RA), see Goldring S R, "Pathogenesis of bone erosions in rheumatoid arthritis". Curr. Opin. Rheumatol. 2002; 14: 406-10. Analysis of joint tissues from patients with RA have provided evidence that cathepsin K positive osteoclasts are the cell types that mediate the focal bone resorption associated with rheumatoid synovial lesion, see Hou, W-S, Li, W, Keyszer, G, Weber, E, Levy, R, Klein, M J, Gravallese, E M, Goldring, S R, Bromme, D, "Comparison of Cathepsin K and S expression within the Rheumatoid and Osteoarthritic Synovium", Arthritis Rheumatism 2002; 46: 663-74. In addition, generalized bone loss is a major cause of morbidity associated with severe RA. The frequency of hip and spinal fractures is substantially increased in patients with chronic RA, see Gould A, Sambrook, P, Devlin J et al, "Osteoclastic activation is the principal mechanism leading to secondary osteoporosis in rheumatoid arthritis". J. Rheumatol. 1998; 25: 1282-9. The utility of cathepsin K inhibitors in the treatment or prevention of resorption in subarticular bone and of generalized bone loss represent a rational approach for pharmacological intervention on the progression of rheumatoid arthritis.

Another embodiment of the invention is a method of treating or preventing the progression of osteoarthritis in a mammal in need thereof, comprising administering to the mammal a therapeutically effective amount of any of the compounds or any of the pharmaceutical compositions described above. It is known in the literature that osteoarthritis (OA) is accompanied with well-defined changes in the joints, including erosion of the articular cartilage surface, peri-articular endochondral ossification/osteophytosis, and subchondral bony sclerosis and cyst formation, see Oettmeier R, Abendroth, K, "Osteoarthritis and bone: osteologic types of osteoarthritis of the hip", Skeletal Radiol. 1989; 18: 165-74. Recently, the potential contribution of subchondral bone sclerosis to the initiation and progression of OA have been suggested. Stiffened subchondral bone as the joint responding to repetitive impulsive loading, is less able to attenuate and distribute forces through the joint, subjecting it to greater mechanical stress across the articular cartilage surface. This in turn accelerates cartilage wear and fibrillate, see Radin, E L and Rose R M, "Role of subchondral bone in the initiation and progression of cartilage damage", Clin. Orthop. 1986; 213: 34-40. Inhibition of excessive subarticular bone resorption by an anti-resorptive agent such as a cathepsin K inhibitor, will lead to inhibition of subchondral bone turnover, thus may have a favorable impact on OA progression.

In addition to the above hypothesis, cathepsin K protein expression was recently identified in synovial fibroblasts, macrophage-like cells, and chondrocytes from synovium and articular cartilage specimens derived from OA patients, see Hou, W-S, Li, W, Keyszer, G, Weber, E, Levy, R, Klein, M J, Gravallese, E M, Goldring, S R, Bromme, D, "Comparison of Cathepsin K and S expression within the Rheumatoid and Osteoarthritic Synovium", Arthritis Rheumatism 2002; 46: 663-74; and Dodd, R A, Connor, J R, Drake, F H, Gowen, M, "Expression of Cathepsin K messenger RNA in giant cells and their precursors in human osteoarthritic synovial tissues". Arthritis Rheumatism 1999; 42: 1588-93; and Konttinen, Y T, Mandelin, J, Li, T-F, Salo, J, Lassus, J et al. "Acidic cysteine endoproteinase cathepsin K in the degeneration of the superficial articular hyaline cartilage in osteoarthritis", Arthritis Rheumatism 2002; 46: 953-60. These recent studies thus implicated the role of cathepsin K in the destruction of collagen type II in the articular cartilage associated with the progression of osteoarthritis. The utility of cathepsin K inhibitors in the treatment or prevention of osteoarthritis as described in this invention thus comprise of two different mechanisms, one is on the inhibition of osteoclast-driven subchondral bone turnover, and two is on the direct inhibition of collagen type II degeneration in the synovium and cartilage of patients with OA.

Another embodiment of the invention is a method of treating cancer in a mammal in need thereof, comprising administering to the mammal a therapeutically effective amount of any of the compounds or any of the pharmaceutical compositions described above. It is known in the literature that cathepsin K is expressed in human breast carcinoma, prostate cancer and chordoma and has matrix degrading capabilities, see Littlewood-Evans A J, Bilbe G, Bowler W B, Farley D, Wlodarski B, Kokubo T, Inaoka T, Sloane J, Evans D B, Gallagher J A, "The osteoclast-associated protease cathepsin K is expressed in human breast carcinoma." Cancer Res 1997 Dec. 1; 57(23):5386-90, Brubaker K D, Vessella R L, True L D, Thomas R, Corey E "Cathepsin K mRNA and protein expression in prostate cancer progression." J Bone Miner Res 2003 18, 222-30, Haeckel C, Krueger S, Kuester D, Ostertag H, Samii M, Buehling F, Broemme D, Czerniak B, Roessner A. "Expression of cathepsin K in chordoma." Hum Pathol 2000 July; 31(7):834-40.

Another embodiment of the invention is a method of treating atherosclerosis in a mammal in need thereof, comprising administering to the mammal a therapeutically effective amount of any of the compounds or any of the pharmaceutical compositions described above. It is known in the literature that cathepsin K is expressed in human atheroma and has significant elastase activity, see Sukhova G K, Shi G P, Simon D I, Chapman H A, Libby P. "Expression of the elastolytic cathepsins S and K in human atheroma and regulation of their production in smooth muscle cells." J Clin Invest 1998 August 102, 576-83. It is also known that the Cat K null mouse when crossed with an ApoE null mouse shows reduced atherosclerotic plaque area and increased resistance to plaque rupture, see E. Lutgens, S. P. M. Lutgens, B. C. G. Faber, S. Heeneman, M. M. J. Gijbels, M. P. J. de Whither, P. Frederik, I. van der Made, D. Black, M. J. A. P. Daemen, K. B. J. M. Cleutjens "Disruption of the Cathepsin K Gene Reduces Atherosclerosis Progression and Induces Plaque Fibrosis but Accelerates Macrophage Foam Cell Formation." Circulation 2006 113:98-107. Increased plaque stability would lead to a decrease in heart attack and stroke in a patient administered a therapeutically effective amount of any of the compounds or any of the pharmaceutical compositions described above.

Another embodiment of the invention is a method of treating obesity in a mammal in need thereof, comprising administering to the mammal a therapeutically effective amount of any of the compounds or any of the pharmaceutical compositions described above. It is known in the literature that cathepsin K mRNA is increased in adipose tissue in several mouse models of obesity and also in adipose tissue of obese human males, see Chiellini C, Costa M, Novelli S E, Amri E Z, Benzi L, Bertacca A, Cohen P, Del Prato S, Friedman J M, Maffei M. "Identification of cathepsin K as a novel marker of adiposity in white adipose tissue," J Cell Physiol 2003, 195, 309-21.

Another embodiment of the invention is a method of treating glaucoma in a mammal in need thereof, comprising administering to the mammal a therapeutically effective amount of any of the compounds or any of the pharmaceutical compositions described above. Cathepsin K is highly expressed in the iris, ciliary body and retinal pigment epithelium, and as such can be useful in the treatment of glaucoma, see Ortega, J., et al., "Gene Expression of Proteases and Protease Inhibitors in the Human Ciliary Epithelium and ODM-2 cells," Exp. Eye Res (1997) 65, 289-299; International Publication WO 2004/058238 (Alcon, Inc.).

Another embodiment of the invention is a method of treating chronic obstructive pulmonary disease in a mammal in need thereof, comprising administering to the mammal a therapeutically effective amount of any of the compounds or any of the pharmaceutical compositions described above. It is known in the literature that cathepsin K plays a role in lung fibrosis, see Buhling, F., et al., "Pivotal role of cathepsin K in lung fibrosis," Am J Pathol. 2004 June; 164(6):2203-16.

Another embodiment of the invention is a method of treating parasitic infections in a mammal in need thereof, comprising administering to the mammal a therapeutically effective amount of any of the compounds or any of the pharmaceutical compositions described above. It is known in the literature that mammalian cathepsins are related to the papain-like cysteine proteases which play an important role in the life cycle of these parasites. Such parasites are involved in the diseases of malaria, American trypanosomiasis, African trypanosomiasis, leishmaniasis, giardiasis, trichomoniasis, amoebiasis, schistosomiasis, fascioliasis, paragonimiasis and intestinal roundworms, see Lecaille F, Kaleta J, Bromme D., Human and parasitic papain-like cysteine proteases: their role in physiology and pathology and recent developments in inhibitor design. Chem Rev 2002 102, 4459-88.

Another embodiment of the invention is a method of treating severe acute respiratory syndrome (SARS) in a mammal in need thereof, comprising administering to the mammal a therapeutically effective amount of any of the compounds or any of the pharmaceutical compositions described above.

Another embodiment of the invention is a method of treating metastatic bone disease in a mammal in need thereof, comprising administering to the mammal a therapeutically effective amount of any of the compounds or any of the pharmaceutical compositions described above. It is known in the literature that osteoclasts are responsible for bone resorption and that bone destruction and hypercalcemia induced by metastatic tumors are carried out by osteoclasts. Accordingly, the inhibition of osteoclasts can prevent bone destruction and bone metastasis, see Miyamoto, T. and Suda, T., "Differentiation and function of osteoclasts," Keio J Med 2003 March; 52(1):1-7.

Another embodiment of the invention is a method of preventing metastatic bone disease in a mammal with a primary tumor that carries a risk of bone metastasis, comprising administering to the mammal a therapeutically effective amount of any of the compounds or any of the pharmaceutical compositions described above. It is described in the literature that compounds that inhibit osteoclasts function can prevent tumor cell adhesion to bone, see S. Boissier, M. Ferreras, O. Peyruchaud, S. Magnetto, F. H. Ebetino, M. Colombel, P. Delmas, J.-M. Delaissé and P. Clézardin "Bisphosphonates Inhibit Breast and Prostate Carcinoma Cell Invasion, an Early Event in the Formation of Bone Metastases" *Cancer Research* 60, 2949-2954, 2000

Another embodiment of the invention is a method of treating hypercalcemia of malignancy or multiple myeloma in a mammal in need thereof, comprising administering to the mammal a therapeutically effective amount of any of the compounds or any of the pharmaceutical compositions described above. It is known in the literature that cathepsin K plays a role in hypercalcemia of malignancy and multiple myeloma, see Faust, J. et al., Multiple myeloma cells and cells of the human osteoclast lineage share morphological and cell surface markers. J Cell Biochem. 1998 Dec. 15; 71(4):559-68; A. lipton, New therapeutic agents for the treatment of bone diseases. Expert Opin Biol Ther. 2005 June; 5(6):817-32.

Another embodiment of the invention is administering to a mammal a therapeutically effective amount of any of the compounds or any of the pharmaceutical compositions described above for the treatment of mammalian diseases associated with cathepsin S including Alzheimer's disease, atherosclerosis, chronic obstructive pulmonary disease, cancer and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogenic immune responses, including, but not limited to, rejection of organ transplants or tissue grafts. It is known in the literature that cathepsin S activity is associated with the above disease states, see Munger J S, Haass C, Lernere C A, Shi G P, Wong W S, Teplow D B, Selkoe D J, Chapman H A. Lysosomal processing of amyloid precursor protein to A beta peptides: a distinct role for cathepsin S. Biochem J 1995 311, 299-305, Sukhova G K, Zhang Y, Pan J H, Wada Y, Yamamoto T, Naito M, Kodama T, Tsimikas S, Witztum J L, Lu M L, Sakara Y, Chin M T, Libby P, Shi G P. Deficiency of cathepsin S reduces atherosclerosis in LDL receptor-deficient mice. J Clin Invest 2003 111, 897-906, Zheng T, Zhu Z, Wang Z, Homer R J, Ma B, Riese R J Jr, Chapman H A Jr, Shapiro S D, Elias J A. Inducible targeting of IL-13 to the adult lung causes matrix metalloproteinase- and cathepsin-dependent emphysema. J Clin Invest 2000 106, 1081-93, Shi G P, Sukhova G K, Kuzuya M, Ye Q, Du J, Zhang Y, Pan J H, Lu M L, Cheng X W, Iguchi A, Perrey S, Lee A M, Chapman H A, Libby P. Deficiency of the cysteine protease cathepsin S impairs microvessel growth. Circ Res 2003 92, 493-500, Nakagawa T Y, Brissette W H, Lira P D, Griffiths R J, Petrushova N, Stock J, McNeish J D, Eastman S E, Howard E D, Clarke S R, Rosloniec E F, Elliott E A, Rudensky A Y. Impaired invariant chain degradation and antigen presentation and diminished collagen-induced arthritis in cathepsin S null mice. Immunity 1999 10, 207-17.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, metastatic bone disease and/or disorders related to cathepsin functioning.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

In the case of tablets for oral use, carriers which are commonly used include lactose and corn starch, and lubricating agents, such as magnesium stearate, are commonly added. For oral administration in capsule form, useful diluents include lactose and dried corn starch. For oral use of a therapeutic compound according to this invention, the selected compound may be administered, for example, in the form of tablets or capsules, or as an aqueous solution or suspension. For oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture.

Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The cathepsin K inhibitors of the present invention can also be administered as solid dispersion formulations which can be made by spray drying or hot melt extrusion processes. The cathepsin K inhibitor is combined with a polymer, thus forming an amorphous system after spray drying. The spray dried amorphous systems are made by combining 10-20% of the cathepsin K inhibitor with 80-90% polymer. The amorphous system is then combined with excipients to form tablets, or combined with water to form a suspension.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The instant compounds are also useful in combination with known agents useful for treating or preventing osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy, and multiple myeloma. Combinations of the presently disclosed compounds with other agents useful in treating or preventing osteoporosis or other bone disorders are within the scope of the invention. A person of ordinary skill in the art would be able to discern which combinations of agents would be useful based on the particular characteristics of the drugs and the disease involved. Such agents include the following: an organic bisphosphonate; a selective estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; calcium, Vitamin D; a synthetic Vitamin D analogue; a Nonsteroidal anti-inflammatory drug; a selective cyclooxygenase-2 inhibitor; an inhibitor of interleukin-1 beta; a LOX/COX inhibitor; and the pharmaceutically acceptable salts and mixtures thereof. A preferred combination is a compound of the present invention and an organic bisphosphonate. Another preferred combination is a compound of the present invention and a selective estrogen receptor modulator. Another preferred combination is a compound of the present invention and an androgen receptor modulator. Another preferred combination is a compound of the present invention and an osteoblast anabolic agent.

"Organic bisphosphonate" includes, but is not limited to, compounds of the chemical formula wherein n is an integer from 0 to 7 and wherein A and X are independently selected from the group consisting of H, OH, halogen, $NH_2$, SH, phenyl, $C_1$-$C_{30}$ alkyl, $C_3$-$C_{30}$ branched or cycloalkyl, bicyclic ring structure containing two or three N, $C_1$-$C_{30}$ substituted alkyl, $C_1$-$C_{10}$ alkyl substituted $NH_2$, $C_3$-$C_{10}$ branched or cycloalkyl substituted $NH_2$, $C_1$-$C_{10}$ dialkyl substituted $NH_2$, $C_1$-$C_{10}$ alkoxy, $C_1$-$C_{10}$ alkyl substituted thio, thiophenyl, halophenylthio, $C_1$-$C_{10}$ alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a $C_3$-$C_{10}$ ring.

In the foregoing chemical formula, the alkyl groups can be straight, branched, or cyclic, provided sufficient atoms are selected for the chemical formula. The $C_1$-$C_{30}$ substituted alkyl can include a wide variety of substituents, nonlimiting examples which include those selected from the group consisting of phenyl, pyridyl, furanyl, pyrrolidinyl, imidazonyl, $NH_2$, $C_1$-$C_{10}$ alkyl or dialkyl substituted $NH_2$, OH, SH, and $C_1$-$C_{10}$ alkoxy.

The foregoing chemical formula is also intended to encompass complex carbocyclic, aromatic and hetero atom structures for the A and/or X substituents, nonlimiting examples of which include naphthyl, quinolyl, isoquinolyl, adamantyl, and chlorophenylthio.

Pharmaceutically acceptable salts and derivatives of the bisphosphonates are also useful herein. Non-limiting examples of salts include those selected from the group consisting alkali metal, alkaline metal, ammonium, and mono-, di-, tri-, or tetra-$C_1$-$C_{10}$-alkyl-substituted ammonium. Preferred salts are those selected from the group consisting of sodium, potassium, calcium, magnesium, and ammonium salts. More preferred are sodium salts. Non-limiting examples of derivatives include those selected from the group consisting of esters, hydrates, and amides.

It should be noted that the terms "bisphosphonate" and "bisphosphonates", as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated. Because of the mixed nomenclature currently in use by those of ordinary skill in the art, reference to a specific weight or percentage of a bisphosphonate compound in the present invention is on an acid active weight basis, unless indicated otherwise herein. For example, the phrase "about 5 mg of a bone resorption inhibiting bisphosphonate selected from the group consisting of alendronate, pharmaceutically acceptable salts thereof, and mixtures thereof, on an alendronic acid active weight basis" means that the amount of the bisphosphonate compound selected is calculated based on 5 mg of alendronic acid.

Non-limiting examples of bisphosphonates useful herein include the following:

Alendronate, which is also known as alendronic acid, 4-amino-1-hydroxybutylidene-1,1-bisphosphonic acid, alendronate sodium or alendronate monosodium trihydrate, 4-amino-1-hydroxybutylidene-1,1-bisphosphonic acid monosodium trihydrate.

Alendronate is described in U.S. Pat. No. 4,922,007, to Kieczykowski et al., issued May 1, 1990; U.S. Pat. No. 5,019, 651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997, all of which are incorporated by reference herein in their entirety.

Cycloheptylaminomethylene-1,1-bisphosphonic acid, YM 175, Yamanouchi (incadronate, formerly known as cimadronate), as described in U.S. Pat. No. 4,970,335, to Isomura et al., issued Nov. 13, 1990, which is incorporated by reference herein in its entirety.

1,1-dichloromethylene-1,1-diphosphonic acid (clodronic acid), and the disodium salt (clodronate, Procter and Gamble), are described in Belgium Patent 672,205 (1966) and J. Org. Chem 32, 4111 (1967), both of which are incorporated by reference herein in their entirety.

1-hydroxy-3-(1-pyrrolidinyl)-propylidene-1,1-bisphosphonic acid (EB-1053).

1-hydroxyethane-1,1-diphosphonic acid (etidronic acid).

1-hydroxy-3-(N-methyl-N-pentylamino)propylidene-1,1-bisphosphonic acid, also known as BM-210955, Boehringer-Mannheim (ibandronate), is described in U.S. Pat. No. 4,927, 814, issued May 22, 1990, which is incorporated by reference herein in its entirety.

1-hydroxy-2-imidazo-(1,2-a)pyridin-3-yethylidene (minodronate).

6-amino-1-hydroxyhexylidene-1,1-bisphosphonic acid (neridronate).

3-(dimethylamino)-1-hydroxypropylidene-1,1-bisphosphonic acid (olpadronate).

3-amino-1-hydroxypropylidene-1,1-bisphosphonic acid (pamidronate).

[2-(2-pyridinyl)ethylidene]-1,1-bisphosphonic acid (piridronate) is described in U.S. Pat. No. 4,761,406, which is incorporated by reference in its entirety.

1-hydroxy-2-(3-pyridinyl)-ethylidene-1,1-bisphosphonic acid (risedronate).

(4-chlorophenyl)thiomethane-1,1-disphosphonic acid (tiludronate) as described in U.S. Pat. No. 4,876,248, to Breliere et al., Oct. 24, 1989, which is incorporated by reference herein in its entirety.

1-hydroxy-2-(1H-imidazol-1-yl)ethylidene-1,1-bisphosphonic acid (zoledronate).

Nonlimiting examples of bisphosphonates include alendronate, cimadronate, clodronate, etidronate, ibandronate, incadronate, minodronate, neridronate, olpadronate, pamidronate, piridronate, risedronate, tiludronate, and zolendronate, and pharmaceutically acceptable salts and esters thereof. A particularly preferred bisphosphonate is alendronate, especially a sodium, potassium, calcium, magnesium or ammonium salt of alendronic acid. Exemplifying the preferred bisphosphonate is a sodium salt of alendronic acid, especially a hydrated sodium salt of alendronic acid. The salt can be hydrated with a whole number of moles of water or non whole numbers of moles of water. Further exemplifying the preferred bisphosphonate is a hydrated sodium salt of alendronic acid, especially when the hydrated salt is alendronate monosodium trihydrate.

It is recognized that mixtures of two or more of the bisphosphonate actives can be utilized.

The precise dosage of the organic bisphosphonate will vary with the dosing schedule, the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. Generally, an appropriate amount of bisphosphonate is chosen to obtain a bone resorption inhibiting effect, i.e. a bone resorption inhibiting amount of the bisphosphonate is administered. For humans, an effective oral dose of bisphosphonate is typically from about 1.5 to about 6000 µg/kg body weight and preferably about 10 to about 2000 µg/kg of body weight. For alendronate monosodium trihydrate, common human doses which are administered are generally in the range of about 2 mg/day to about 40 mg/day, preferably about 5 mg/day to about 40 mg/day. In the U.S. presently approved dosages for alendronate monosodium trihydrate are 5 mg/day for preventing osteoporosis, 10 mg/day for treating osteoporosis, and 40 mg/day for treating Paget's disease.

In alternative dosing regimens, the bisphosphonate can be administered at intervals other than daily, for example once-weekly dosing, twice-weekly dosing, biweekly dosing, and twice-monthly dosing. In a once weekly dosing regimen, alendronate monosodium trihydrate would be administered at dosages of 35 mg/week or 70 mg/week.

"Selective estrogen receptor modulators" refers to compounds which interfere or inhibit the binding of estrogen to the receptor, regardless of mechanism. Examples of estrogen receptor modulators include, but are not limited to, estrogen, progestogen, estradiol, droloxifene, raloxifene, lasofoxifene, TSE-424, tamoxifen, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

An "estrogen receptor beta modulator" is a compound that selectively agonizes or antagonizes estrogen receptor beta (ERβ Agonizing ERβ increases transcription of the tryptophan hydroxylase gene (TPH, the key enzyme in serotonin synthesis) via an ERβ mediated event. Examples of estrogen receptor beta agonists can be found in PCT International publication WO 01/82923, which published on Nov. 8, 2001, and WO 02/41835, which published on May 20, 2002, both of which are hereby incorporated by reference in their entirety.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"An inhibitor of osteoclast proton ATPase" refers to an inhibitor of the proton ATPase, which is found on the apical membrane of the osteoclast, and has been reported to play a significant role in the bone resorption process. This proton pump represents an attractive target for the design of inhibitors of bone resorption which are potentially useful for the treatment and prevention of osteoporosis and related metabolic diseases. See C. Farina et al., "Selective inhibitors of the osteoclast vacuolar proton ATPase as novel bone antiresorptive agents," DDT, 4: 163-172 (1999)), which is hereby incorporated by reference in its entirety.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

Lactone I

Open-Acid II

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenz-imidazole, diethylamine, piperazine, and tris(hydroxymethyl)aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

As used above, "integrin receptor antagonists" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. H. N. Lode and coworkers in PNAS USA 96: 1591-1596 (1999) have observed synergistic effects between an antiangiogenic αv integrin antagonist and a tumor-specific antibody-cytokine (interleukin-2) fusion protein in the eradication of spontaneous tumor metastases. Their results suggested this combination as having potential for the treatment of cancer and metastatic tumor growth. $\alpha_v\beta_3$ integrin receptor antagonists inhibit bone resorption through a new mechanism distinct from that of all currently available drugs. Integrins are heterodimeric transmembrane adhesion receptors that mediate cell-cell and cell-matrix interactions. The α and β integrin subunits interact non-covalently and bind extracellular matrix ligands in a divalent cation-dependent manner. The most abundant integrin on osteoclasts is $\alpha_v\beta_3$ ($>10^7$/osteoclast), which appears to play a rate-limiting role in cytoskeletal organization important for cell migration and polarization. The $\alpha_v\beta_3$ antagonizing effect is selected from inhibition of bone resorption, inhibition of restenosis, inhibition of macular degeneration, inhibition of arthritis, and inhibition of cancer and metastatic growth.

"An osteoblast anabolic agent" refers to agents that build bone, such as PTH. The intermittent administration of parathyroid hormone (PTH) or its amino-terminal fragments and analogues have been shown to prevent, arrest, partially reverse bone loss and stimulate bone formation in animals and humans. For a discussion refer to D. W. Dempster et al., "Anabolic actions of parathyroid hormone on bone," Endocr Rev 14: 690-709 (1993). Studies have demonstrated the clinical benefits of parathyroid hormone in stimulating bone formation and thereby increasing bone mass and strength. Results were reported by R M Neer et al., in New Eng J Med 344 1434-1441 (2001).

In addition, parathyroid hormone-related protein fragments or analogues, such as PTHrP-(1-36) have demonstrated potent anticalciuric effects [see M. A. Syed et al., "Parathyroid hormone-related protein-(1-36) stimulates renal tubular calcium reabsorption in normal human volunteers: implications for the pathogenesis of humoral hypercalcemia of malignancy," JCEM 86: 1525-1531 (2001)] and may also have potential as anabolic agents for treating osteoporosis.

"Vitamin D" includes, but is not limited to, vitamin $D_3$ (cholecalciferol) and vitamin $D_2$ (ergocalciferol), which are naturally occurring, biologically inactive precursors of the hydroxylated biologically active metabolites of vitamin D: 1α-hydroxy vitamin D; 25-hydroxy vitamin D, and 1α,25-dihydroxy vitamin D. Vitamin $D_2$ and vitamin $D_3$ have the same biological efficacy in humans. When either vitamin $D_2$ or $D_3$ enters the circulation, it is hydroxylated by cytochrome $P_{450}$-vitamin D-25-hydroxylase to give 25-hydroxy vitamin D. The 25-hydroxy vitamin D metabolite is biologically inert and is further hydroxylated in the kidney by cytochrome P450-monooxygenase, 25 (OH) D-1α-hydroxylase to give 1,25-dihydroxy vitamin D. When serum calcium decreases, there is an increase in the production of parathyroid hormone (PTH), which regulates calcium homeostasis and increases plasma calcium levels by increasing the conversion of 25-hydroxy vitamin D to 1,25-dihydroxy vitamin D.

1,25-dihydroxy vitamin D is thought to be responsible for the effects of vitamin D on calcium and bone metabolism. The 1,25-dihydroxy metabolite is the active hormone required to maintain calcium absorption and skeletal integrity. Calcium homeostasis is maintained by 1,25-dihydroxy vitamin D by inducing monocytic stem cells to differentiate into osteoclasts and by maintaining calcium in the normal range, which results in bone mineralization by the deposition of calcium hydroxyapatite onto the bone surface, see Holick, M F, Vitamin D photobiology, metabolism, and clinical applications, In: DeGroot L, Besser H, Burger H G, eg al., eds. *Endocrinology*, $3^{rd}$ ed., 990-1013 (1995). However, elevated levels of 1α,25-dihydroxy vitamin $D_3$ can result in an increase of calcium concentration in the blood and in the abnormal control of calcium concentration by bone metabolism, resulting in hypercalcemia. 1α,25-dihydroxy vitamin $D_3$ also indirectly regulates osteoclastic activity in bone metabolism and elevated levels may be expected to increase excessive bone resorption in osteoporosis.

"Synthetic vitamin D analogues" includes non-naturally occurring compounds that act like vitamin D.

"Nonsteroidal anti-inflammatory drugs" or NSAIDs, inhibit the metabolism of arachidonic acid to proinflammatory prostaglandins via cyclooxygenase (COX)-1 and COX-2. Nonlimiting examples of NSAIDs include: aspirin, ibuprofen, naproxen, diclofenac, etodolac, fenoporfen, flubiprofen, indomethacin, ketoprofen, ketorolac, meloxicam, nabumetone, oxaprozin, piroxicam, sulindac, tolmetin, diflunisal, meclofenamate and phenylbutazone.

A "selective cyclooxygenase-2 inhibitor," or COX-2 inhibitor, refers to a type of nonsteroidal anti-inflammatory drug (NSAID), that inhibit the COX-2 coenzyme, which contributes to pain and inflammation in the body. Nonlimiting examples of COX-2 inhibitor include: celecoxib, etoricoxib, parecoxib, rofecoxib, valdecoxib and lumiracoxib.

An "inhibitor of interleukin-1 beta" or IL-1β refers to in inhibitors of IL-1, which is a soluble factor produced by monocytes, macrophages, and other cells which activates T-lymphocytes and potentiates their response to mitogens or antigens. Nonlimiting examples of IL-1B inhibitors include diacerein and rhein.

A "LOX/COX inhibitor" refers to an inhibitor or all three of the major enzymes involved in arachidonic acid pathway—namely, 5-LOX, COX-1 and COX-2. A nonlimiting example of a LOX/COX inhibitor is licofelone.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents. The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The terms "treating" or "treatment" of a disease as used herein includes: inhibiting the disease, i.e., arresting or reducing the development of the disease or its clinical symptoms; or relieving the disease, i.e., causing regression of the disease or its clinical symptoms. The terms "preventing" or "prevention" of a disease as used herein includes causing the clinical symptoms of the disease not to develop in a mammal that may be exposed to or predisposed to the disease but does not yet experience or display symptoms of the disease.

The term "bone resorption," as used herein, refers to the process by which osteoclasts degrade bone.

The present invention also encompasses a pharmaceutical composition useful in the treatment of osteoporosis or other bone disorders, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for a cathepsin dependent condition. Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. A medicament typically contains from about 0.01 mg to about 500 mg of the active ingredient, preferably, from about 1 mg to about 100 mg of active ingredient. For oral administration, the compositions are preferably provided in the form of tablets containing 2.5 mg, 5 mg, 10 mg, 20 mg, 25 mg, 35 mg, 40 mg, 50 mg, 80 mg, 100 mg and 200 mg of the active ingredient for the symptomatic adjustment of the dosage to the patient to be treated. A medicament typically contains from about 2.5 mg to about 200 mg of the active ingredient, specifically, 2.5 mg, 5 mg, 10 mg, 20 mg, 25 mg, 35 mg, 40 mg, 50 mg, 80 mg, 100 mg and 200 mg of active ingredient. The compounds of the present invention may be administered in a single daily dose, or the total daily dosage may be administered in divided doses of two, three or four times daily. Advantageously, the cathepsin K inhibitor may be administered in a single weekly dose. Alternatively, the cathepsin K inhibitor may be administered in a biweekly, twice monthly or monthly dose. Intravenously, the most preferred doses will range from about 0.1 to about 10 mg/kg/minute during a constant rate infusion. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The compounds of the present invention can be used in combination with other agents useful for treating cathepsin-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating cathepsin-mediated conditions includes in principle any combination with any pharmaceutical composition useful for treating disorders related to estrogen functioning.

The scope of the invention therefore encompasses the use of the instantly claimed compounds in combination with a second agent selected from: an organic bisphosphonate; a selective estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; calcium, Vitamin D; a synthetic Vitamin D analogue; a Nonsteroidal anti-inflammatory drug; a selective cyclooxygenase-2 inhibitor; an inhibitor of interleukin-1 beta; a LOX/COX inhibitor and the pharmaceutically acceptable salts and mixtures thereof.

These and other aspects of the invention will be apparent from the teachings contained herein.

DEFINITIONS

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted.

When any variable (e.g. X) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring carbon atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

The present invention also includes N-oxide derivatives and protected derivatives of compounds of Formula I. For example, when compounds of Formula I contain an oxidizable nitrogen atom, the nitrogen atom can be converted to an N-oxide by methods well known in the art. Also when compounds of Formula I contain groups such as hydroxy, carboxy, thiol or any group containing a nitrogen atom(s), these groups can be protected with a suitable protecting groups. A comprehensive list of suitable protective groups can be found in T. W. Greene, Protective Groups in Organic Synthesis, John Wiley & Sons, Inc. 1981, the disclosure of which is incorporated herein by reference in its entirety. The protected derivatives of compounds of Formula I can be prepared by methods well known in the art.

The pharmaceutically acceptable salts of the compounds of this invention include the conventional non-toxic salts of the compounds of this invention as formed inorganic or organic acids. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic and the like. The preparation of the pharmaceutically acceptable salts described above and other typical pharmaceutically acceptable salts is more fully described by Berg et al., "Pharmaceutical Salts," J. Pharm. Sci., 1977:66:1-19, hereby incorporated by reference. The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

For purposes of this specification, the following abbreviations have the indicated meanings:
AcCl=acetyl chloride
i-BuOC(O)Cl=isobutyl chloroformate
(Boc)$_2$O=boc anhydride
CrO$_3$=chromium trioxide
DAST=diethylaminosulfur trifluoride
DCM=dichloromethane
EDC=1-ethyl-3-[3-dimethylaminopropyl]carbodiimide hydrochloride
EtOH=ethanol
H$_5$IO$_6$=periodic acid
HOBT=hydroxybenzotriazole hydrate
KOH=potassium hydroxide
K$_2$CO$_3$=potassium carbonate
MgI=magnesium iodide
NaBH$_4$=sodium borohydride
NMM=N-methyl morpholine
Pd(OAc)$_2$=palladium acetate
p-(Tos)$_2$O=p-toluenesulfonic anhydride
THF=tetrahydrofuran
Zn(BH$_4$)$_2$=zinc borohydride
MeOH=methanol
MgSO$_4$=magnesium sulfate
sat. aq.=saturated aqueous
tlc=thin layer chromatography
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl The following schemes and examples describe the synthesis of selected compounds of the current invention and are included for illustrative purposes and does not limit the scope of the invention in any way.

Example 1

Preparation of D6-Odanacatib

Step 1. Benzyl (3S)-3-[(tert-butoxycarbonyl)amino]-4-hydroxybutanoate (2)

N-(tert-butoxycarbonyl)-L-aspartic acid 4-benzyl ester (1.23 g, 3.80 mmol) was dissolved in dimethoxyethane (3.6 mL) in a flame-dried flask. The solution was cooled to −5 to −10° C. N-methylmorpholine (0.422 mL, 3.84 mmol) was then added dropwise, followed by a slow addition of isobutyl chloroformate (0.525 mL, 3.9 mmol) while the reaction temperature was maintained below −10° C. The mixture was aged for 30 minutes. The solids were quickly filtered and washed with dimethoxyethane (3.6 mL). The filtrate was cooled to −50° C. and a solution of sodium borohydride (0.18 g, 4.76 mmol) in water (1.8 mL) was added slowly while the reaction temperature was maintained between −30° C. and −15° C. Water (20 mL) was then added such that the reaction mixture temperature was maintained below −15° C. The reaction mixture was extracted with ethyl acetate (3×5 mL), washed with cold 0.1N HCl, then saturated sodium bicarbonate solution and then brine. The organic phase was dried with magnesium sulfate. Evaporated to dryness to yield an oil that crystallizes upon standing. LC-MS m/z=332 (M+Na$^+$).

Step 2. Benzyl [(4S)-2-oxo-1,3-oxazolidin-4-yl]acetate (3)

The alcohol 2 (500 mg, 1.616 mmol) was azeotroped with toluene, and then dissolved in dichloroethane (5 mL). Pyridine (1.44 mL, 17.78 mmol) was added and the mixture was cooled to 0° C. Anhydrous p-toluenesulfonic anhydride (580 mg, 1.778 mmol) was added and the mixture was warmed to room temperature and stirred for 1 hour. A condenser was adapted to the reaction flask and the mixture heated to 90° C. for two hours. Added additional 0.5 equivalents (290 mg) of p-toluenesulfonic anhydride and heated at 90° C. overnight. The mixture was cooled, diluted with dichloromethane and washed with 1 N HCl (2×3 mL), then water. The organic layer was dried with sodium sulfate and filtered over a small silica plug, rinsing with ethyl acetate. The solvents were removed in vacuo to afford an oil that crystallizes. LC-MS m/z=253 (M+NH$_4^+$).

Step 3. (4S)-4-[3,3,3-trideuterio-2-hydroxy-2-(trideuteriomethyl)propyl]-1,3-Oxazolidin-2-one (4)

A Grignard reagent was prepared in a flame-dried flask with [D$_3$]-methyl iodide (2.314 ml, 37.2 mmol) and magnesium turnings (1.033 g, 42.5 mmol) in the presence of a trace of Iodine in 15 mL of diethyl ether. Once formed, it was diluted with 20 mL of tetrahydrofuran and 20 mL of toluene while cooling to −20° C. A solution of the benzyl ester 3 (2.5 g, 10.63 mmol) in tetrahydrofuran (10 mL) was added dropwise. The mixture was stirred at −20° C. for two hours and then quenched by slow addition of a mixture of 4 mL acetic acid in 20 mL water. This mixture was stirred at 0° C. allowing it to warm up to room temperature overnight. The aqueous layer was separated and the organic phase extracted with water twice. This aqueous solution was purified by RP-HPLC-MS with 3-50% MeCN/water (0.1% TFA) on a Waters SunFire C18 column. The combined HPLC streams were lyophilized to obtain pure product. LC-MS m/z=166 (M+H).

Step 4. (4S)-4-[3,3,3-trideuterio-2-fluoro-2-(trideuteriomethyl)propyl]-1,3-oxazolidin-2-one (5)

A solution of the alcohol 4 (1.068 g, 6.46 mmol) in dichloromethane (10 mL) was added dropwise to a solution of DAST ((diethylamino)sulfur trifluoride, 0.871 ml, 6.59 mmol) in dichloromethane that was cooled to −70° C. in a Teflon vial. The alcohol vial was rinsed with 2 mL of dichloromethane and the rinses added to the reaction mixture. The mixture was stirred while allowing to warm to room temperature for three hours. This reaction mixture was then carefully added to saturated bicarbonate (10 mL) cooled to 0° C. Separated the organic phase and extracted the aqueous phase with dichloromethane (2×3 mL). The combined organic phase was dried over sodium sulfate and filtered over a silica plug. The solvent was concentrated to dryness to yield the product in quantitative crude yield, which was used as is for the next reaction. LC-MS m/z=168 (M+H).

Step 5. Tert-butyl N-[(1S)-4,4,4-trideuterio-3-fluoro-1-(hydroxymethyl)-3 (trideuteriomethyl)butyl]carbamate (6)

The fluoro derivative 5 (1.25 g, 7.48 mmol) was dissolved in 35 mL of 90% ethanol/water. Potassium hydroxide (1.258 g, 22.43 mmol) was added and the mixture heated at reflux for five hours. The ethanol was evaporated off, then the mixture azeotroped with toluene (3×50 mL). The residue was suspended in dichloromethane and filtered over a celite pad. The celite was rinsed with dichloromethane (3×20 mL). The filtrate was evaporated to dryness to obtain a dark yellow oil. This residue was redissolved in dichloromethane (15 mL) and cooled to 0° C. under nitrogen. Di-tert-butyl dicarbonate (1.909 mL, 8.22 mmol) dissolved in 2 mL dichloromethane was then added dropwise, followed by slow addition of triethylamine (1.094 mL, 7.85 mmol). The mixture was stirred at room temperature for 7 hours, until starting material was consumed by TLC and LC-MS. The dichloromethane was removed under vacuum. The residue was redissolved in ethyl acetate (100 mL), washed with brine (100 mL), then saturated ammonium chloride (2×50 mL) and then brine (100 mL). The organic phase was dried with magnesium sulfate and filtered over a silica pad. The organic phase was evaporated to dryness to yield a light yellow thick oil which was used as is for the next reaction. LC-MS: Molecular ion was not found. The ion fragments of the isotope-labeled product were matched against those of an authentic unlabeled sample.

Step 6. N-[(2S)-2-(tert-butoxycarbonylamino)-5,5,5-trideuterio-4-fluoro-4-(trideuteriomethyl)]pentanoic acid ($D_6$-fluoro-L-leucine, 7)

A stock solution of $H_5IO_6/CrO_3$ was prepared by dissolving $H_5IO_6$ (11.4 g, 50 mmol) and $CrO_3$ (23 mg, 1.2 mol %) in wet acetonitrile to a volume of 114 mL. The Boc-alcohol 6 (241 mg, 1 mmol) was dissolved in 6 mL acetonitrile and cooled to 0° C. 6.38 mL of the stock solution were added dropwise, and the mixture stirred at 0° C. for 30 minutes. The reaction mixture was quenched by adding 6 mL of 0.4M $Na_2HPO4$ solution. Extracted with toluene (3×20 mL). Washed the organic phase with 50:50 water/brine (10 mL), saturated sodium thiosulfate (5 mL) and brine (5 mL). Dried the organic phase with magnesium sulphate and filtered over a small silica pad. Concentrated the solvent to dryness. Used as is for the next reaction. LC-MS m/z=254 (M−H).

Step 7. Ethyl N-[(2S)-2-(tert-butoxycarbonylamino)-5,5,5-trideuterio-4-fluoro-4-(trideuteriomethyl)]pentanoate ($D_6$-fluoro-L-leucine ethyl ester, 8)

The $D_6$-fluoroleucine 7 (187 mg, 0.732 mmol) was dissolved in 5 mL anhydrous ethanol and cooled to 0° C. Acetyl chloride (156 µl, 2.197 mmol) was added dropwise, slowly, and the mixture stirred while allowing to warm up to room temperature overnight. The mixture was evaporated to dryness and then azeotroped with toluene. The mixture was then resuspended in methyl tert-butyl ether and added 100 mg of potassium carbonate to break the salt. Washed organic phase with brine and evaporated to dryness to yield desired product. LC-MS m/z=184 (M+H).

Step 8. (2S)-2-[[(1S)-1-(4-bromophenyl)-2,2,2-trifluoro-ethyl]amino]-5,5,5-trideuterio-4-fluoro-4-(trideuteriomethyl)pentanoic acid (10)

The 1-(4-bromophenyl)-2,2,2-trifluoro-ethanone 9 (80 mg, 0.316 mmol) and fluoroleucine ester 8 (63.7 mg, 0.348 mmol) were combined with potassium carbonate (87 mg, 0.632 mmol) in 1 mL of methanol and heated at 50° C. for 4 hours, then stirred to room temperature overnight to form the imine intermediate. In another flame-dried flask, sodium borohydride (43.1 mg, 1.138 mmol) was added to 0.5M zinc chloride (1138 µl, 0.569 mmol) in dimethoxyethane (1 mL) and stirred overnight. The zinc borohydride thus formed was then cooled to −45° C. and the imine mixture added dropwise, slowly, to maintain the temperature. The imine vial was rinsed with 2 mL anhydrous acetonitrile and added to the mixture dropwise. Stirred at −45° C. for 15 minutes, and then stirred at 0° C. for 1 hour. The mixture was then carefully quenched with acetone (340 uL) and stirred for 30 minutes, then poured over ice-cold 1N HCl (2 mL) and extracted with ethyl acetate. Washed the organic phase with brine and dried over magnesium sulfate. Filtered and evaporated to dryness. Used the crude (which was obtained in quantitative crude yield) as is for the next reaction. LC-MS m/z=392 (M+H).

Step 9. (2S)-2-[[(1S)-1-(4-bromophenyl)-2,2,2-trifluoro-ethyl]amino]-N-(1-cyanocyclopropyl)-5,5,5-trideuterio-4-fluoro-4-(trideuteriomethyl)pentanamide (12)

The crude intermediate 10 (124 mg, 0.316 mmol) was dissolved in dimethylacetamide (1 mL), then the aminocyclopropanecarbonitrile HCl 11 (45.0 mg, 0.379 mmol), hydroxybenzotriazole hydrate (48.4 mg, 0.316 mmol), EDC.HCl (72.7 mg, 0.379 mmol) and N-methyl morpholine (69.5 µl, 0.632 mmol) were charged. The mixture was stirred at 35° C. for 3 hours, after which time LC-MS indicated the starting material was consumed. The mixture was then cooled to room temperature and partitioned with ethyl acetate and water. Washed the organic phase with 0.1 N HCl (2 mL), then diluted sodium bicarbonate solution (2 mL) and brine (3 mL). The solvent was dried with magnesium sulfate and concentrated to dryness and used as is for the next reaction. LC-MS m/z=456 (M+H).

Step 10. (2S)—N-(1-cyanocyclopropyl)-5,5,5-trideuterio-4-fluoro-4-(trideuteriomethyl)-2-[[(1S)-2,2,2-trifluoro-1-[4-(4-methylsulfonylphenyl)phenyl]ethyl]amino]pentanamide ([$D_6$]Odanacatib, 14)

The crude bromide 12 (180 mg, 0.394 mmol) and (4-methylsulfonylphenyl)boronic acid 13 (103 mg, 0.513 mmol) were dissolved in 2.5 mL of tetrahydrofuran in a flame-dried vial. The mixture was degassed thoroughly by bubbling nitrogen. Palladium acetate (4.43 mg, 0.020 mmol) and S-Phos (16.19 mg, 0.039 mmol) were then added and the mixture degassed again. Then a solution of 1M potassium phosphate tribasic (789 µl, 0.789 mmol) was added. The vial was degassed and sealed. The reaction mixture was heated at 60° C. with stirring overnight. The mixture was partitioned with ethyl acetate and water. The organic phase was washed with brine and dried over magnesium sulfate, filtered and concentrated to dryness. The product was purified using RP-HPLC with Phenomenex Luna PFP using isocratic 52% MeCN/ 0.1% Formic acid. The combined pure fractions were lyophilized to yield the desired product 14 over three synthetic steps. LC-MS m/z=532 (M+H).

$^1$H NMR (500 MHz, $CDCl_3$): δ 8.04 (m, 2H), 7.78 (m, 2H), 7.66 (m, 2H), 7.49 (m, 2H), 7.43 (s, 1H), 4.17 (quin, J=6.7 Hz, 1H), 3.60 (dt, J=9.0, 3.2 Hz, 1H), 3.11 (s, 3H), 2.99 (m, 1H), 2.07 (ddd, J=31.6, 15.4, 3.1 Hz, 1H), 1.96 (td, J=15.3, 9.0 Hz, 1H), 1.47 (m, 2H), 1.07 (m, 1H), 0.92 (m, 1H).

$^{13}$C NMR (125 MHz, $CDCl_3$): δ 174.51, 145.77, 140.65, 139.98, 134.59, 129.48, 128.30 (x2), 128.28, 125.43 (q, $J_{CF}$=282.8 Hz), 119.65, 96.78 (d, $J_{CF}$=163.1 Hz), 63.50 (q, $J_{CF}$=28.8 Hz), 59.12, 44.83, 43.54 (d, $J_{CF}$=19.8 Hz), 20.26, 16.96, 16.55.

Pharmaceutical Composition

As a specific embodiment of this invention, 50 mg of (2S)—N-(1-cyanocyclopropyl)-5,5,5-trideuterio-4-fluoro-4-(trideuteriomethyl)-2-[[(1S)-2,2,2-trifluoro-1-[4-(4-methylsulfonylphenyl)phenyl]ethyl]amino]pentanamide is formulated with sufficient finely divided lactose to provide a total amount of 580 to 590 mg to fill a size 0, hard-gelatin capsule.

The compounds disclosed in the present application exhibited activity in the following assay. In addition, the compounds disclosed in the present application have an enhanced pharmacological profile relative to previously disclosed compounds.

Scheme 1 describes the synthesis of odanacatib wherein the terminal methylsulfone is deuterated.

Assays

Rhesus IV Pharmacokinetics

The study was conducted in male rhesus monkeys (n=4) via the intravenous route using a deuteriated ($D_6$-Odanacatib, or $D_6$-ODN) and non-deuteriated ($D_0$-Odanacatib, or $D_0$-ODN) forms of odanacatib. The dosing solution was prepared in DMSO at a concentration of 7.5 mg/mL and the dose volume was 0.1 mL/kg. Each monkey was administered a 0.75 mg/kg dose each of $D_6$-ODN and $D_0$-ODN as a mixture. Animals were fasted overnight prior to dosing. The dose was administered via the saphenous vein. Blood was obtained from the femoral or saphenous vein using either direct stick or an in-dwelling temporary catheter and placed in blood tubes coated with $K_3$EDTA. Plasma was obtained by centrifugation and placed in a 96 well Matrix box. Plasma was stored at −70° C. until analysis.

The concentrations of $D_6$-ODN and $D_0$-ODN in plasma were determined by LC-MS/MS in the positive ion mode using the Turbo Ion Spray interface. Odanacatib and the internal standard ($^{13}C_{12}$—ODN) were isolated from plasma (100 μL) by liquid-liquid extraction using MTBE. The extract was evaporated (37° C.) to dryness and the residue reconstituted with 50/50 acetonitrile/water containing 1 mM ammonium format (250 μL), and 2 μL aliquots were injected into the LC-MS/MS system. Quantification was based on selected reaction monitoring of the following precursor/product ion pairs: m/z 526.3→313.0 ($D_0$-ODN); m/z 532.2→313.2 ($D_6$-ODN); m/z 538.3→325.2 ($^{13}C_{12}$-MK-0822). The lower limit of quantitation was 0.48 nM.

Pharmacokinetic parameters were obtained using non-compartmental methods (Watson®). The plasma clearance ($CL_P$) was calculated as the IV dose divided by the area under the plasma concentration versus time curve ($AUC_{0-\infty}$). AUC was determined using logarithmic trapezoidal interpolation.

As shown in the table below, the deuterated odanacatib ($D_6$-ODN) has a 3-fold higher exposure, 3-fold lower clearance and 4-fold longer half-life when compared to the non-deuterated odanacatib ($D_0$-ODN):

| | Time (hours) | $D_0$-ODN (nM) | $D_6$-ODN (nM) |
|---|---|---|---|
| | 0.00 | | |
| | 0.08 | 1024.6197 | 893.6923 |
| | 0.25 | 947.0634 | 838.9307 |
| | 0.50 | 872.0364 | 792.9969 |
| | 1.00 | 853.9769 | 830.9187 |
| | 4.00 | 462.0605 | 633.2716 |
| | 8.00 | 249.8222 | 632.7467 |
| | 12.00 | 129.8319 | 515.2637 |
| | 24.00 | 14.5281 | 272.7977 |
| | 30.00 | 6.2188 | 207.9300 |
| | 48.00 | 1.2193 | 70.7012 |
| | 72.00 | | 28.3614 |
| | 96.00 | | 13.8245 |
| $AUC_{(0-x)}$ (nM * hr) | | 5714 | 17700 |
| $AUC_{(0-\infty)}$ (nM * hr) | | 5726 | 18030 |
| % AUC Extrap. | | 0.25 | 1.7 |
| $Vd_{ss}$ (L/kg) | | 1.9 | 1.7 |
| $C_0$ (nM) | | 1077 | 933 |
| Cl (mL/min/kg) | | 4.6 | 1.4 |
| t½ (hr) | | 3.7 | 16.0 |

Rhesus Pharmacokinetics with Crystalline and Spray-Dried Formulations

The pharmacokinetic evaluation was carried out following oral administration to monkeys of the following ODN forms and formulations: $D_6$-ODN spray-dried formulation (A), $D_6$-ODN conventional formulation (B), $D_0$-ODN spray-dried formulation (C) and $D_0$-ODN conventional formulation (D). The plasma exposure (AUC) was 47.2±24.8 μM*hr, 14.7±4.8 μM*hr, 13.5±11.8 μM*hr and 7.5±5.8 μM*hr, for drug form/formulation A, B, C and D, respectively. Thus, the data show that the exposure of ODN is increased by both deuterium substitution (14.7 μM*hr vs. 7.5 μM*hr) and formulating as a spray-dried material (13.5 μM*hr vs. 7.5 μM*hr). However, combining deuterium substitution and spray-drying provides an even greater boost in exposure (6.3-fold increase) compared to that obtained by either spray-drying (1.8-fold) or deuterium substitution (2.0-fold). The 24 hr concentration was also increased by 3.1-fold and 7.7-fold by deuterium substitution and spray-drying plus deuterium substitution, respectively. Deuterium substitution increased the plasma elimination half-life of ODN by about 2.5-fold.

Experimental Details

The deuterated analog of odanacatib ($D_6$-ODN) as well as ODN ($D_0$-ODN) were prepared either as spray-dried or conventional (crystalline) formulations for pharmacokinetic study in monkeys. The spray-dried form was suspended in water, while the crystalline drug was dissolved in Imwitor:Tween for oral administration to monkeys. Spray-dried $D_6$-ODN (A), crystalline $D_6$-ODN (B), spray-dried $D_0$-ODN (C) and crystalline $D_0$-ODN (D) were dosed to monkeys (n=4) in a cross-over fashion. Each monkey was administered a ~2.5 mg/kg dose each of forms B and D as a mixture in period one, and forms C and A were then dosed after a washout period. Blood was obtained from the femoral or saphenous vein using either direct stick or an in-dwelling temporary catheter and placed in blood tubes coated with $K_3$EDTA. Plasma was obtained by centrifugation and placed in a 96 well Matrix box. Plasma was stored at −70° C. until analysis.

The concentrations of $D_6$-ODN and $D_0$-ODN in plasma were determined by LC-MS/MS in the positive ion mode using the Turbo Ion Spray interface. ODN and the internal standard ($^{13}C_{12}$-ODN) were isolated from plasma (100 μL) by liquid-liquid extraction using MTBE. The extract was evaporated (37° C.) to dryness and the residue reconstituted with 50/50 acetonitrile/water containing 1 mM ammonium formate (250 μL), and 2 μL aliquots were injected into the LC-MS/MS system. Quantification was based on selected reaction monitoring of the following precursor/product ion pairs: m/z 526.3→313.0 ($D_0$-ODN); m/z 532.2→313.2 ($D_6$-ODN); m/z 538.3→325.2 ($^{13}C_{12}$-ODN). The lower limit of quantitation was 1.9 nM.

Pharmacokinetic parameters were obtained using non-compartmental methods (Watson®). The results from this study are shown in the following table and FIG. 2.

Average Plasma Concentrations and Pharmacokinetic Parameters in Monkeys

Figure 1:
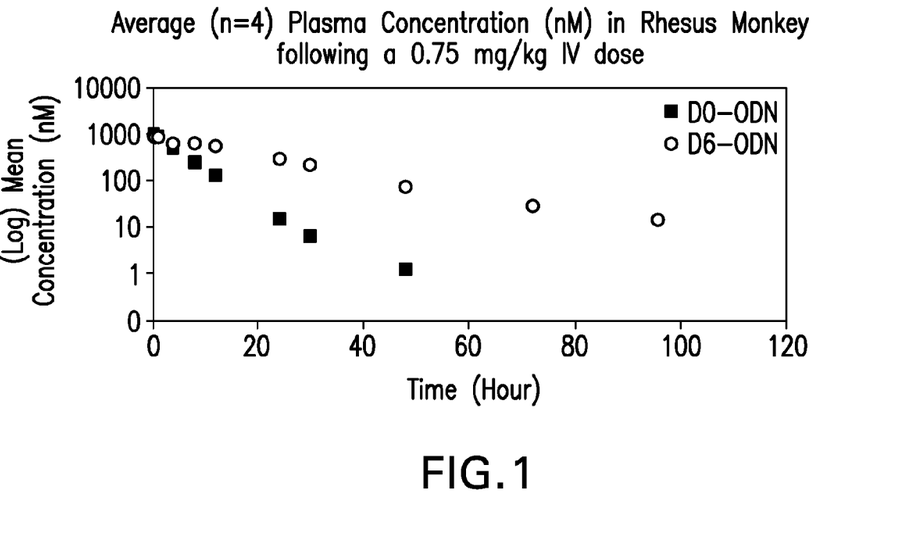
FIG. 1: Average Plasma Concentration in Rhesus Monkeys. The average (n=4) Plasma Concentration (nM) of D0-odanacatib and D6-odanacatib in Rhesus Monkey following a 0.75 mg/kg IV dose of D0-odanacatib (D0-ODN) and D6-odanacatib (D6-ODN) is shown.
Figure 2:
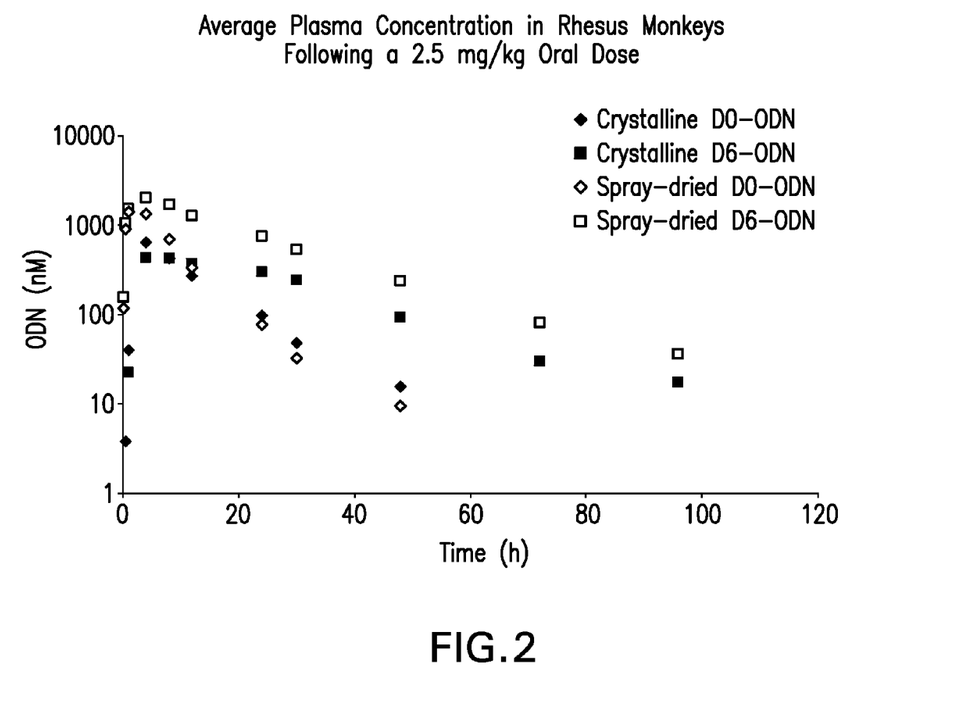
FIG. 2: Average Plasma Concentration in Rhesus Monkeys Following a 2.5 mg/kg Oral Dose. The average Plasma Concentration (nM) of crystalline D0-odanacatib, crystalline D6-odanacatib, spray-dried D0-odanacatib and spray-dried D6-odanacatib in Rhesus Monkey following a 2.5 mg/kg oral dose of each is shown.

| Time (hr) | $D_0$-ODN Crystalline (D) (nM) | $D_0$-ODN Spray-dried (C) (nM) | $D_6$-ODN Crystalline (B) (nM) | $D_6$-ODN Spray-dried (A) (nM) |
|---|---|---|---|---|
| 0.00 | | | | |
| 0.25 | | 116.3 | | 155.1 |
| 0.50 | 3.8 | 891.7 | | 1040.1 |
| 1.00 | 40.1 | 1418.9 | 22.6 | 1534.0 |
| 4.00 | 644.1 | 1329.6 | 435.1 | 2022.7 |
| 8.00 | 424.0 | 685.3 | 424.2 | 1691.5 |

-continued

| Time (hr) | $D_0$-ODN Crystalline (D) (nM) | $D_0$-ODN Spray-dried (C) (nM) | $D_6$-ODN Crystalline (B) (nM) | $D_6$-ODN Spray-dried (A) (nM) |
|---|---|---|---|---|
| 12.00 | 268.6 | 333.1 | 370.9 | 1265.0 |
| 24.00 | 98.7 | 76.8 | 303.4 | 749.8 |
| 30.00 | 48.4 | 32.8 | 243.8 | 535.4 |
| 48.00 | 15.4 | 9.6 | 92.0 | 234.5 |
| 72.00 |  |  | 29.7 | 81.0 |
| 96.00 |  |  | 17.3 | 35.8 |
| $AUC_{0-\infty}$ (μM * hr) | 7.5 ± 5.8 | 13.5 ± 11.8 | 14.7 ± 4.8 | 47.2 ± 24.8 |
| $C_{max}$ (μM) | 0.6 ± 0.3 | 1.6 ± 1.2 | 0.5 ± 0.1 | 2.0 ± 0.9 |
| $t_{max}$ (hr) | 4.0 ± 0.0 | 1.8 ± 1.5 | 6.0 ± 2.3 | 4.0 ± 0.0 |
| $t_{1/2}$ (hr) | 5.6 ± 1.7 | 5.7 ± 1.8 | 13.6 ± 1.2 | 14.1 ± 2.7 |
| $C_{24\,hr}$ (μM) | 0.098 ± 0.129 | 0.077 ± 0.073 | 0.303 ± 0.131 | 0.750 ± 0.361 |
| $C_{72\,hr}$ (μM) | BLQ | BLQ | 0.030 ± 0.018 | 0.081 ± 0.078 |

BLQ = below the limit of quantitation; limit of quantitation = 1.9 nM

What is claimed is:

1. A compound of the formula:

wherein the compound has a deuterium atom at each position designated as deuterium, and any atom not designated as deuterium is present at its natural abundance; or a pharmaceutically acceptable salt thereof.

2. A pharmaceutical composition comprising a compound according to claim 1 and a pharmaceutically acceptable carrier.

3. A method of treating osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, atherosclerosis, obesity, glaucoma, chronic obstructive pulmonary disease, metastatic bone disease, hypercalcemia of malignancy or multiple myeloma in a mammal in need of such treatment with a therapeutically effective amount of a compound according to claim 1.

4. A pharmaceutical composition comprising a compound of claim 1 and an agent selected from the group consisting of: an organic bisphosphonate, a selective estrogen receptor modulator, an estrogen receptor beta modulator, an androgen receptor modulator, an inhibitor of osteoclast proton ATPase, an inhibitor of HMG-CoA reductase, an integrin receptor antagonist, or an osteoblast anabolic agent, calcium, vitamin D, a synthetic Vitamin D analogue, a Nonsteroidal anti-inflammatory drug, a selective cyclooxygenase-2 inhibitor, an inhibitor of interleukin-1 beta, a LOX/COX inhibitor and the pharmaceutically acceptable salts and mixtures thereof.

5. A method of treating osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, atherosclerosis, obesity, glaucoma, chronic obstructive pulmonary disease, metastatic bone disease, hypercalcemia of malignancy or multiple myeloma in a mammal in need of such treatment with a compound of claim 1 and an agent selected from the group consisting of: an organic bisphosphonate, a selective estrogen receptor modulator, an androgen receptor modulator, an inhibitor of osteoclast proton ATPase, an inhibitor of HMG-CoA reductase, an integrin receptor antagonist, an osteoblast anabolic agent, calcium, vitamin D, a synthetic Vitamin D analogue, a Nonsteroidal anti-inflammatory drug, a selective cyclooxygenase-2 inhibitor, an inhibitor of interleukin-1 beta, a LOX/COX inhibitor and the pharmaceutically acceptable salts and mixtures thereof.

6. A compound of the formula:

wherein the compound has a deuterium atom at each position designated as deuterium, and any atom not designated as deuterium is present at its natural abundance.

* * * * *